United States Patent [19]
Chen

[11] Patent Number: 5,575,774
[45] Date of Patent: Nov. 19, 1996

[54] STRUCTURE OF SAFETY HYPODERMIC SYRINGE

[76] Inventor: Long-Hsiung Chen, 5F, No. 91-3, Chung Cheng Road, Section 1,, Taipei, Taiwan

[21] Appl. No.: 547,358

[22] Filed: Oct. 24, 1995

[51] Int. Cl.⁶ .................................................. A61M 5/00
[52] U.S. Cl. ............................................ 604/110; 604/195
[58] Field of Search ................................. 604/110, 187, 604/192, 195, 198, 263, 218

[56] References Cited

U.S. PATENT DOCUMENTS

| | | | |
|---|---|---|---|
| 4,804,370 | 2/1989 | Haber et al. | 604/110 X |
| 4,846,808 | 7/1989 | Haber et al. | 604/195 |
| 5,104,378 | 4/1992 | Haber et al. | 604/110 |
| 5,295,973 | 3/1994 | Chen | 604/110 X |

*Primary Examiner*—John D. Yasko
*Attorney, Agent, or Firm*—Bacon & Thomas

[57] ABSTRACT

A safety hypodermic syringe in which the needle holder has an arrowhead-like rear retaining hole; the rubber stopper has an arrowhead-like retainer rod that can be forced into engagement with the retaining hole of the needle holder for permitting the needle holder with the needle cannula to be pulled backwards to the inside of the barrel by the plunger; the plunger can be disconnected from the rubber stopper and then inserted into the front end of the barrel to deform the needle cannula when the needle cannula is received on the inside of the barrel.

4 Claims, 3 Drawing Sheets

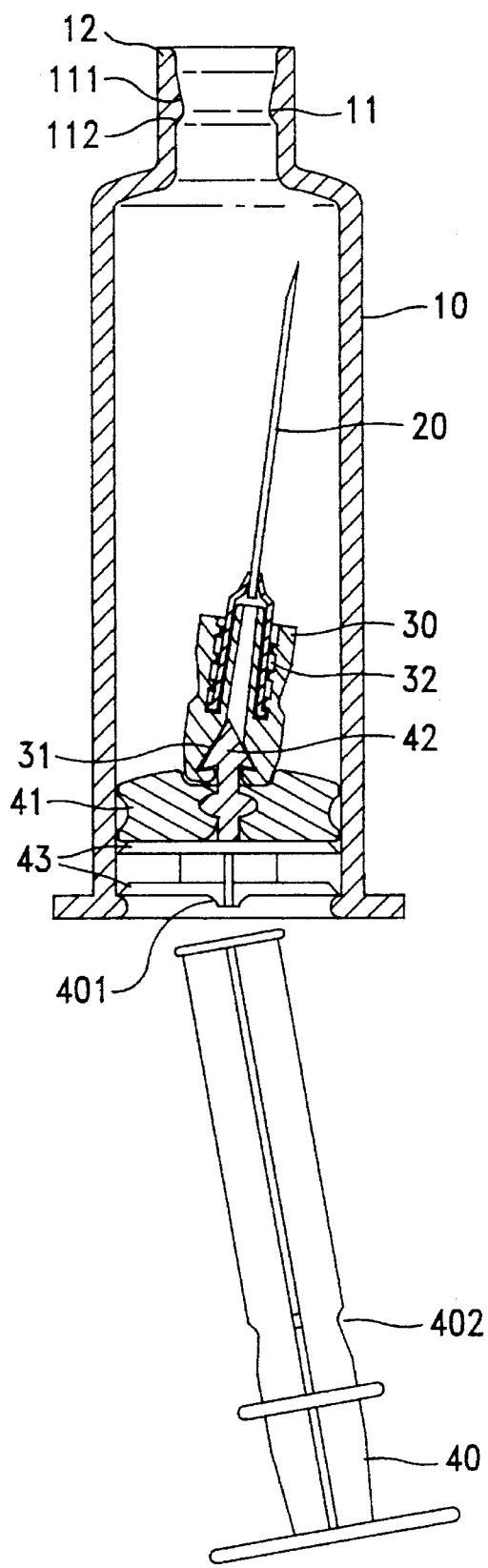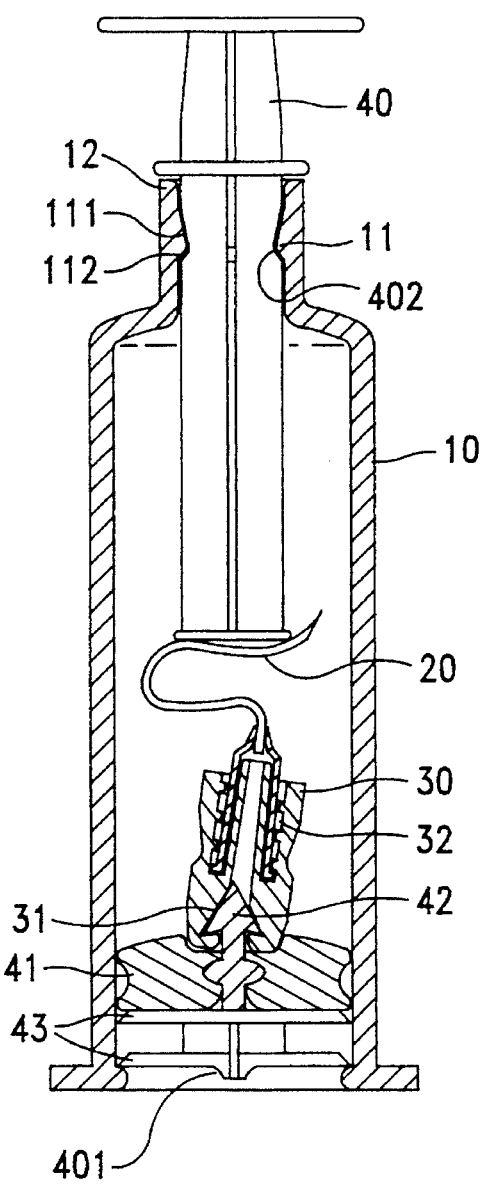
FIG.4
FIG.5

STRUCTURE OF SAFETY HYPODERMIC SYRINGE

BACKGROUND OF THE INVENTION

The present invention relates to hypodermic syringes, and relates more particularly to a safety hypodermic syringe which permits the needle holder with the needle cannula to be pulled backwards to the inside of the barrel by the plunger after injection, and permits the plunger to be disconnected from the rubber stopper and then inserted into the front end of the barrel to deform the needle cannula inside the barrel.

The needle cannula of a hypodermic syringe must be damaged after its use, and then properly disposed of. Taiwan patent publication no. 210509 discloses a safety hypodermic syringe which permits the needle cannula to be pulled backwards to the inside of the barrel after its use. However, this structure of safety hypodermic syringe must be used with a specially designed needle cannula. Another drawback of this structure of safety hypodermic syringe is that the deformed needle cannula will still project out of the barrel if the needle cap is disconnected. Taiwan patent publication no. 212301 discloses another structure of safety hypodermic syringe. This structure of safety hypodermic syringe still cannot be used with regular commercially available needle cannula. Taiwan patent application no. 82218049 discloses still another structure of safety hypodermic syringe. This structure of safety hypodermic syringe is designed to adapt any of a variety of commercially available needle cannulas. However, because the needle holder has an opening which is not sealed after the needle cannula has been moved to the inside of the barrel, the needle cannula will still project out of the barrel.

SUMMARY OF THE INVENTION

The present invention has been accomplished to provide a safety hypodermic syringe which eliminates the aforesaid drawbacks. According to one aspect of the present invention, the needle holder has an arrowhead-like retaining hole; the rubber stopper has an arrowhead-like retainer rod that can be forced into engagement with the retaining hole of the needle holder for permitting the needle holder with the needle cannula to be pulled backwards to the inside of the barrel by the plunger. According to another aspect of the present invention, the plunger is connected to the rubber stopper by a connecting member, which has a connecting tip connected to the plunger that can be broken to let the plunger be disconnected from the rubber stopper and then inserted into the front end of the barrel to deform the needle cannula when the needle cannula is received on the inside of the barrel. According to still another aspect of the present invention, the front end of the barrel has an inside flange which defines a front sloping wall and a rear sloping wall of different angles such that the needle holder can be moved backwards to the inside of the barrel, but is stopped from being moved forwards to the outside of the front end of the barrel.

BRIEF DESCRIPTION OF THE DRAWINGS

FIG. 4 shows the connecting tip of the connecting member broken, and the plunger disconnected from the connecting member according to the present invention;

FIG. 5 shows the plunger inserted into the front neck of the barrel, and the needle cannula deformed according to the present invention.

DETAILED DESCRIPTION OF THE PREFERRED EMBODIMENT

Figure 1:
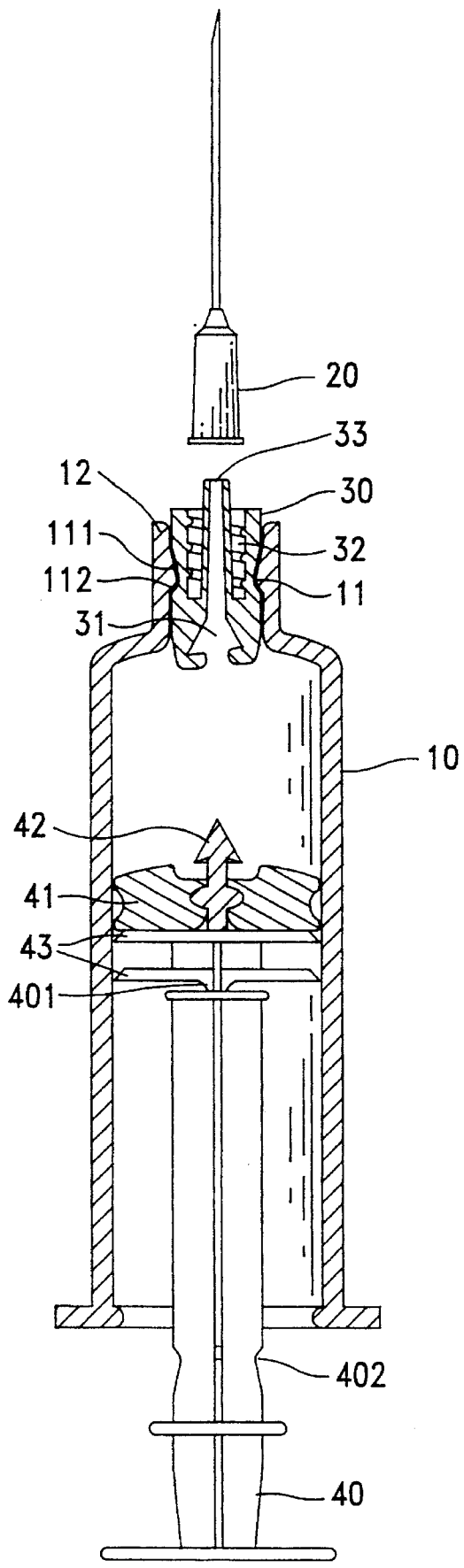
FIG. 1 is a sectional view showing a safety hypodermic syringe according to the present invention.

Referring to FIG. 1, the barrel, referenced by 10, comprises an inside flange 11 raised around the inside wall of the front neck 12 thereof. A needle holder 30 is inserted into the front neck 12 of the barrel 10 and retained in place by the inside flange 11 to hold the needle cannula, referenced by 20. The inside flange 11 has a front sloping wall 111 of small slope and a rear sloping wall 112 of different angles. The front sloping wall 111 and the rear sloping wall 112 are so designed that the needle holder 30 can be pulled backwards into the inside of the barrel 10 but cannot be pushed forwardly out of the front neck 12 of the barrel 10. The needle holder 30 comprises a longitudinal center through hole 33, which imparts a passage between the needle cannula 20 and the holding space of the barrel 10, an inner thread 32 around the longitudinal center through hole 33 for mounting the needle cannula 20, and an arrowhead-like retaining hole 31 at the rear end of the longitudinal center through hole 33 remote from the needle cannula 20. The plunger, referenced by 40, has a locating groove 402 around the periphery near the rear end. The front end of the plunger 40 is connected to a connecting member 43. The connecting member 43 has a connecting tip 401 connected to the front end of the plunger 40. The connecting tip 401 can be easily broken so that the plunger 40 can be disconnected from the connecting member 43. The connecting member 43 may be variously shaped. As an example of the present invention, the connecting member 43 has a plurality of circular flange around the periphery fitting the inner diameter of the barrel 10. A rubber stopper 41 is fixedly secured to the connecting member 43 at the front side remote from the plunger 40. The rubber stopper 41 has an arrowhead-like retainer rod 42 which can be forced into engagement with the arrowhead-like retaining hole 31 of the needle holder 30.

Figure 2:
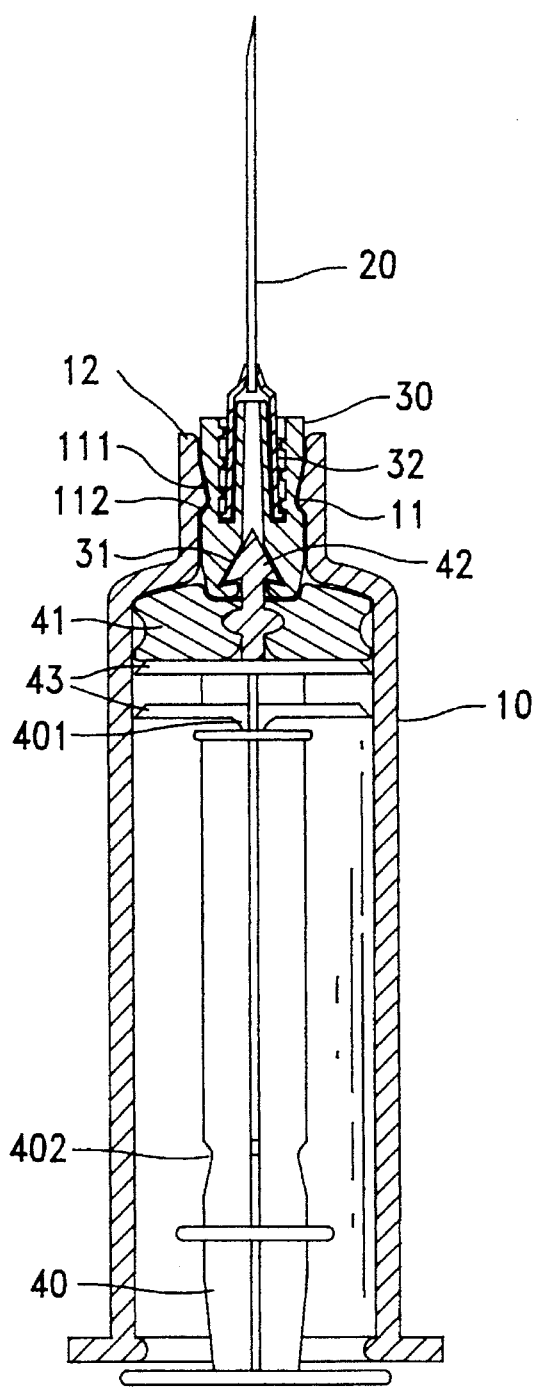
FIG. 2 shows the plunger moved forwards to the inside of the barrel, and the retainer rod of the rubber stopper forced into engagement with the retaining hole of the needle holder according to the present invention.
Figure 3:
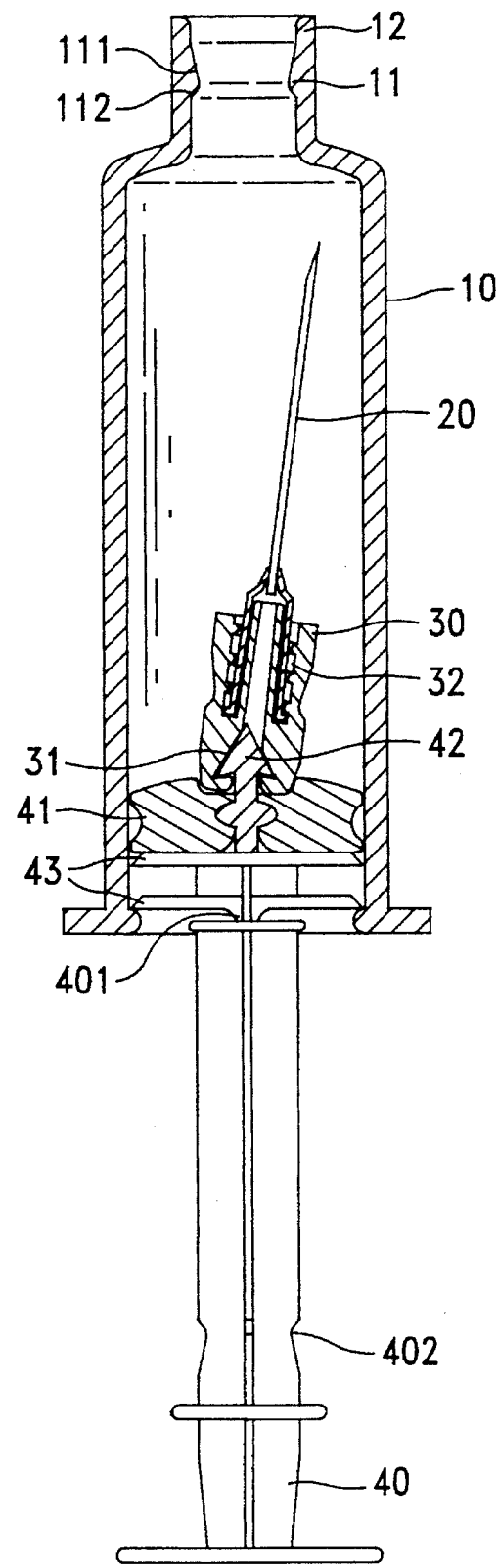
FIG. 3 shows the needle holder and the needle cannula received on the inside of the barrel according to the present invention.

Referring to FIGS. from 2 to 5, when the plunger 40 is moved forwards to the inside of the barrel 10, the liquid medicine is completely squeezed out of the barrel 10 through the needle cannula 20, and at the same time the arrowhead-like retainer rod 42 of the rubber stopper 41 is forced into engagement with the arrowhead-like retaining hole 31 of the needle holder 30 (see FIG. 2). When the plunger 40 is pulled backwards, the needle holder 30 with the needle cannula 20 are pulled backwards to the inside of the barrel 10 (see FIG. 3). Because the arrowhead-like retaining hole 31 slightly slopes from the longitudinal center axis of the needle holder 30, the needle holder 30 and the needle cannula 20 tilt when they are moved to the inside of the barrel 10. When the connecting member 43 is stopped at the rear end of the barrel 10, the plunger 40 is disconnected from the connecting member 43 by breaking the connecting tip 401 (see FIG. 4). Then, the plunger 40 is inserted into the front neck 12 of the barrel 10 to deform the needle cannula 20. When the needle cannula 20 is deformed, the locating groove 402 of the plunger 40 is engaged with the inside flange 11 of the front neck 12 of the barrel 10, and therefore the plunger 40 is firmly retained to the front neck 12 of the barrel 10.

It is to be understood that the drawings are designed for purposes of illustration only, and are not intended as a definition of the limits and scope of the invention disclosed. For example, the retaining hole 31 can be made of conical shape, or in the form of a triangular pyramid; the profile of the front end of the retainer rod 42 fits the configuration of the retaining hole 31 for positive engagement.

I claim:

1. A safety hypodermic syringe comprising a barrel having a front neck and an inside flange inside said front neck, a needle holder inserted into said front neck of said barrel and retained in place by said inside flange of said front neck of said barrel, a needle cannula fastened to said needle holder, a plunger moved in said barrel, a rubber stopper connected to said plunger by a connecting member, wherein said inside flange of said front neck of said barrel has a front sloping wall of small slope and a rear sloping wall of different angles for permitting said needle holder to be pulled backwards to an inside of said barrel and for stopping said needle holder from being forced forwards out of said front neck of said barrel; said needle holder comprises a longitudinal center through hole, which imparts a passage between said needle cannula and said barrel, an inner thread around said longitudinal center through hole for mounting said needle cannula, and a rear retaining hole at one end of said longitudinal center through hole remote from said needle cannula; said connecting member has a connecting tip connected to said plunger that can be broken to let said plunger be disconnected from said connecting member; said rubber stopper has a retainer rod at a front end thereof fitting said retaining hole of said needle holder, said retaining rod being forced into engagement with said retaining hole of said needle holder when said rubber stopper is moved to said front neck of said barrel by said plunger, for permitting said needle holder with said needle cannula to be pulled backwards to said inside of said barrel by said plunger; said plunger can be inserted into said front neck of said barrel to deform said needle cannula when said needle holder and said needle cannula are moved to said inside of said barrel and said plunger is disconnected from the connecting tip of said connecting member; said plunger has a locating groove around a periphery of said plunger for engagement with said inside flange of said front neck of said barrel when it is inserted into front end of said barrel to deform said needle cannula.

2. The safety hypodermic syringe of claim 1 wherein said retaining hole of said needle holder is made of arrowhead-like shape, and slopes from the longitudinal center axis of said needle holder in one direction.

3. The safety hypodermic syringe of claim 1 wherein said retainer rod of said rubber stopper is shaped like an arrowhead fitting said retaining hole of said needle holder.

4. The safety hypodermic syringe of claim 1 wherein said connecting member has at least one circular flange around said periphery fitting an inner diameter of said barrel.

* * * * *